(12) United States Patent
Lee

(10) Patent No.: US 11,497,702 B2
(45) Date of Patent: Nov. 15, 2022

(54) COMPOSITION FOR PREVENTING OR TREATING SCARS

(71) Applicant: Ho Seog Lee, Seoul (KR)

(72) Inventor: Ho Seog Lee, Seoul (KR)

( * ) Notice: Subject to any disclaimer, the term of this patent is extended or adjusted under 35 U.S.C. 154(b) by 95 days.

(21) Appl. No.: 16/622,640

(22) PCT Filed: May 29, 2018

(86) PCT No.: PCT/KR2018/006073
§ 371 (c)(1),
(2) Date: Dec. 13, 2019

(87) PCT Pub. No.: WO2019/027132
PCT Pub. Date: Feb. 7, 2019

(65) Prior Publication Data
US 2021/0137819 A1 May 13, 2021

(30) Foreign Application Priority Data
Jul. 31, 2017 (KR) .................. 10-2017-0097127

(51) Int. Cl.
| | |
|---|---|
| *A61K 8/891* | (2006.01) |
| *A61K 33/24* | (2019.01) |
| *A61K 8/04* | (2006.01) |
| *A61K 8/19* | (2006.01) |
| *A61K 8/26* | (2006.01) |
| *A61K 8/27* | (2006.01) |
| *A61K 8/29* | (2006.01) |
| *A61K 8/58* | (2006.01) |
| *A61K 8/67* | (2006.01) |
| *A61Q 1/02* | (2006.01) |
| *A61Q 19/00* | (2006.01) |

(52) U.S. Cl.
CPC .............. *A61K 8/891* (2013.01); *A61K 8/042* (2013.01); *A61K 8/19* (2013.01); *A61K 8/26* (2013.01); *A61K 8/27* (2013.01); *A61K 8/29* (2013.01); *A61K 8/585* (2013.01); *A61K 8/678* (2013.01); *A61K 33/24* (2013.01); *A61Q 1/02* (2013.01); *A61Q 19/007* (2013.01); *A61K 2800/432* (2013.01)

(58) Field of Classification Search
None
See application file for complete search history.

(56) References Cited

U.S. PATENT DOCUMENTS

| | | |
|---|---|---|
| 5,188,831 A | 2/1993 | Nicoll et al. |
| 2007/0059263 A1 | 3/2007 | Taniguchi et al. |
| 2007/0060666 A1 | 3/2007 | Taniguchi et al. |
| 2010/0196454 A1 | 8/2010 | Keller |
| 2015/0086496 A1 | 3/2015 | Wu et al. |

FOREIGN PATENT DOCUMENTS

| | | |
|---|---|---|
| JP | H07165534 A | 6/1995 |
| JP | 2010-520809 A | 6/2010 |
| JP | 2010520890 A | 6/2010 |
| KR | 10-1991-0019596 A | 12/1991 |
| KR | 10-2004-0061734 A | 7/2004 |
| KR | 10-2008-0038622 A | 5/2008 |
| KR | 10-1210371 B1 | 12/2012 |
| KR | 10-2016-0084825 A | 7/2016 |
| WO | 95/09598 A1 | 4/1995 |
| WO | 2009/109887 A1 | 12/2008 |

OTHER PUBLICATIONS

Kyung (KR101210371), Google Patents Machine Translation, accessed May 20, 2021 (Year: 2021).*
European Search Report issued in corresponding application No. 18840708.4, dated Mar. 4, 2021.

* cited by examiner

*Primary Examiner* — Melissa L Fisher
(74) *Attorney, Agent, or Firm* — Maschoff Brennan

(57) ABSTRACT

The present invention relates to a composition for preventing or treating scars and a preparation method therefor. The composition, according to one aspect, comprises a pigment and silicone oil, and may be stably formulated into a formulation adequate for spreading on the skin, and may inhibit the formation of scars or reduce already existing scars by forming a membrane on the skin, and has an effect whereby scars may be concealed by the pigment stably dispersed in the composition.

1 Claim, 1 Drawing Sheet

COMPOSITION FOR PREVENTING OR TREATING SCARS

TECHNICAL FIELD

The present invention relates to a composition for preventing or treating a scar and a preparation method therefor.

BACKGROUND ART

A skin is mainly classified into three layers of epidermis, dermis, and subcutaneous tissue in a sequence from the outside. The skin, as a primary barrier for a human body, protects organs inside the body from changes in temperature and humidity, ultraviolet rays, and other physical and chemical external stimuli, and plays an important role for maintaining homeostasis such as body temperature control. The epidermis of constituent layers of the skin plays an important role for preventing moisture inside the human body from evaporating. The epidermis is classified into a cornified layer, a granular layer, a spinous layer, and a basal layer in a sequence from the outside, in which cells in the cornified layer serve like bricks, and intercellular lipids between keratinocytes serve as mortars to constitute the skin barrier. Particularly, the epidermal layer has an ability to move cells, thereby serving to heal a wound.

Meanwhile, a scar is a general concept and generic name for signifying morphological and histopathological appearance changes in a normal skin tissue due to various damages. The scar is a normal and essential physiological response during natural repair of the wound or injury surface and is a result of the wound healing process. The scar refers to a tissue having abnormal defects due to loss of a normal tissue viability and loss of a normal skin tissue structure or physiological function. The scar spoils aesthetic appearance of a surface of a human body and deteriorates physiological functions of related organs or tissues.

Since scar treatment agents that have conventionally been used generally include silicone and have a transparent appearance, the scar or wound cannot be concealed. Thus, there is an inconvenience to additionally attach a sheet for concealing the scar or wound after applying the silicone scar treatment agent in order to prevent the aesthetic appearance of the skin surface from being spoiled.

Accordingly, there are needs for studies on stable formulations including a pigment material not to spoil the aesthetic appearance of the skin surface such that the scar or wound can be covered and the scar can be treated without toxicity.

DETAILED DESCRIPTION OF THE INVENTION

Technical Problem

One aspect provides a skin external composition for preventing or treating a scar, which includes pigment and silicone oil.

Another aspect provides a pharmaceutical composition for preventing or treating a scar, which includes pigment and silicone oil.

Another aspect provides a cosmetic composition for preventing or treating a scar, which includes pigment and silicone oil.

Another aspect provides a preparation method of a skin external composition, which includes: obtaining a first phase including silicone oil (S1); obtaining a second phase by mixing and dispersing the silicone oil and the pigment (S2); and mixing and dispersing the first phase and the second phase (S3).

Technical Solution

One aspect provides a skin external composition for preventing or treating a scar, which includes pigment and silicone oil.

In the specification herein, the term "scar" may refer to a fibrous tissue that replaces a normal tissue destroyed by injury or disease. A damaged outer layer of the skin is healed by reconstructing tissues and, in this case, the scar may be insignificantly formed. However, when a thick layer of tissue under the skin is damaged, the reconstruction of the damaged tissue is more complicated. The body accumulates collagen fibers (proteins naturally produced by the body), and thus usually generates a distinct scar.

The scar may be a hypertrophic scar, a keloid scar, an atrophic scar, a stretch mark, or a combination thereof.

The hypertrophic scar is an uplift scar that remains within a boundary of an original lesion, and generally may degrade naturally after an initial injury. The hypertrophic scar is hard, uplifted, red, itching, tender, and contracted. The above scars typically occur after burn injuries on a torso or limb. Clinically and histologically, the hypertrophic scar is very similar to the keloid scar. Unlike keloids, the hypertrophic scar expands while pushing a boundary portion of the scar, but the keloid scar infiltrates surrounding tissues. The hypertrophic scar matures and flattens as time passes. The hypertrophic scar represents the same whorl-type hyalin bundle of collagen as keloid, and has vasa and cells more than those of normal scars.

The keloid scar is a benign fibrous growth of the dermis generated after skin trauma. The keloid scar protrudes upward from a skin surface and extends beyond the boundary of the original lesion. These scars are permanent and do not degrade as time passes. The keloid may be sometimes cosmetically unpleasant and may be accompanied by pain.

The atrophic scar is flat and pressed downward from a surrounding skin. The atrophic scar is generally small and sometimes serrated or rounded with an inverted center. The atrophic scar may be formed due to surgery, trauma, acne and varicella.

The stretch mark usually occurs within three weeks after surgery when a fine line of a surgical scar is gradually stretched and widened. The stretch mark, typically, is a flat, faint and soft asymptomatic scar often seen after knee or shoulder surgery.

In the specification, the term "wound" refers to tissues cut, torn, broken, burned, or traumatized, or refers to injury to a human body arising from a disorder or disease that causes the above symptoms. The wound may be an open wound having open wound or a closed wound without an open surface. One example of the wound may be injury at epidermis of a skin; at dermis; at epidermis and dermis; or at epidermis, dermis and a subcutaneous fat layer. In addition, an example of the wound may include cuts, incisions (such as surgical incisions), abrasions, lacerations, fractures, contusions, burns, or amputations. The wound may be selected from the group consisting of chronic wound, acute wound, surgical wound, orthopedic wound, trauma wound, combat wound, and a combination thereof. In addition, the wound may be caused by another disease. For example, the wound may be due to fibrosis, diabetes, diabetic ulcer, autoimmune skin disease, abrasion, laceration, incision, contusion, contusion, puncture, exfoliation, burn, ulcer, bedsore, or a combination thereof.

In the specification herein, the term "treat" of a scar may refer to healing the scar in a shorter time compared to natural healing.

The scar treatment may include improvement and/or alleviation of a scar or a disease relevant to the scar. In addition, the scar treatment may refer to healing and/or regenerating damaged tissues due to the wound. The scar treatment may include a skin regeneration. In addition, the treatment may include maintaining an original composition of the damaged tissues. In addition, the treatment may include promoting healing and/or regeneration of the damaged tissues while minimizing complications of a disease associated with the wound and/or scars.

The skin external composition reduces an occurrence or severity of a scar on a skin, or both thereof without deteriorating normal wound healing. In addition, compared to a control group without the above composition, the skin external composition can effectively remove the scar on the skin from a subject by reducing at least one of a wound size, a scar area, and a collagen formation in the wound. In addition, the skin external composition has excellent scar hiding ability because it can effectively cover the wound or scar on a surface of the skin.

In the skin external composition, the pigment may include at least one selected from the group consisting of titanium dioxide, zinc oxide, iron oxide, aluminum hydroxide, ultramarine, ferric ferrocyanide, ferric ammonium ferrocyanide, chromium oxide green, chromium hydroxide green, mica, carbon black, manganese violet, and carmine, although not limited thereto.

When the pigment is included, the composition may conceal the scar or wound on the skin.

The skin external composition according to one embodiment may include pigment of about 1 wt % to about 30 wt %, about 1 wt % to about 25 wt %, about 1 wt % to about 23 wt %, about 1 wt % to about 20 wt %, about 1 wt % to about 19 wt %, about 1 wt % to about 19.5 wt %, about 1 wt % to about 19.3 wt %, about 1 wt % to about 19.1 wt %, about 1 wt % to about 19 wt %, about 3 wt % to about 30 wt %, about 3 wt % to about 25 wt %, about 3 wt % to about 23 wt %, about 3 wt % to about 20 wt %, about 3 wt % to about 19 wt %, about 3 wt % to about 19.5 wt %, about 3 wt % to about 19.3 wt %, about 3 wt % to about 19.1 wt %, about 3 wt % to about 19 wt %, about 5 wt % to about 30 wt %, about 5 wt % to about 25 wt %, about 5 wt % to about 23 wt %, about 5 wt % to about 20 wt %, about 5 wt % to about 19 wt %, about 5 wt % to about 19.5 wt %, about 5 wt % to about 19.3 wt %, about 5 wt % to about 19.1 wt %, about 5 wt % to about 19 wt %, about 8 wt % to about 30 wt %, about 8 wt % to about 25 wt %, about 8 wt % to about 23 wt %, about 8 wt % to about 20 wt %, about 8 wt % to about 19 wt %, about 8 wt % to about 19.5 wt %, about 8 wt % to about 19.3 wt %, about 8 wt % to about 19.1 wt %, about 8 wt % to about 19 wt %, about 10 wt % to about 30 wt %, about 10 wt % to about 25 wt %, about 10 wt % to about 23 wt %, about 10 wt % to about 20 wt %, about 10 wt % to about 19 wt %, about 10 wt % to about 19.5 wt %, about 10 wt % to about 19.3 wt %, about 10 wt % to about 19.1 wt %, or about 10 wt % to about 19 wt % based on the total weight of the composition.

When the pigment is out of the above range, for example, when the pigment is included too little, an effect of concealing the scar may be insufficient, and when the pigments are included too much, an appearance of the skin may be spoiled due to the pigment deposited on the skin. For example, when an amount of iron oxide is about 2.5% or more by weight based on the total weight of the composition, the pigmentation on the skin may be realized.

The pigment may be dispersed in the silicone oil. In one embodiment of the invention, the pigment may be dispersed in the silicone oil before mixed with the silicone oil.

In one embodiment according to the invention, the dispersion may be carried out by a milling process. The pigment is dispersed in the silicone oil by the milling process, so that the pigment may be uniformly dispersed and ground in the composition to form a stable formulation, and improve applicability and spreadability without clumping when applied onto the skin.

In the skin external composition, the silicone oil may be colorless silicone oil. Since the colorless silicone oil cannot conceal scars due to lack of concealment when applied to the scars, any colorless silicone oil to conceal the skin or scar may be used without limitation after the silicone oil according to one embodiment is formulated together with the pigment. The silicone oil may include at least one selected from the group consisting of dimethicone, polysilicone-11, polysilicone-15, polysilicone-8, polysilicone-17, hydrogen dimethicone, lauryl dimethicone, cyclopentasiloxane, cyclohexasiloxane, trisiloxane, methyl trimethicone, phentyl methicone, dimethicone copolyol, dimethicone copolyol acetate, silicone glycol copolyol, dimethiconeol, methyl polysiloxane, methyl phenyl polysiloxane, dimethicone copolyol methyl ether, methylcyclopolysiloxane, dimethyl polysiloxane, hexamethyl di siloxanes, and caprylylmethylpolysiloxanes, although not limited thereto.

The composition includes the silicone oil to form a membrane on the skin, so that the scar can be prevented or treated.

The skin external composition according to one embodiment may include silicone oil of about 70 wt % to about 99 wt %, about 70 wt % to about 95 wt %, about 70 wt % to about 90 wt %, about 70 wt % to about 85 wt %, about 70 wt % to about 80 wt %, about 75 wt % to about 99 wt %, about 75 wt % to about 95 wt %, about 75 wt % to about 90 wt %, about 75 wt % to about 85 wt %, or about 75 wt % to about 80 wt % based on the total weight of the composition.

When the pigment is out of the above range, the pigment may not be uniformly dispersed or may be agglomerated, and thus the applicability may be deteriorated, or the effect of preventing or treating the scar may be deteriorated.

The skin external composition may further include a sunscreen. The sunscreen may be included at about 5% to about 20% by weight based on the total composition. When the sunscreen is further included in the composition, a direct exposure of ultraviolet rays on the wound or scar may be prevented, so that the effect of preventing or treating the wound or scar may be promoted. Titanium dioxide or zinc oxide in the pigment may serve as the sunscreen. An example of the sunscreen may include ethylhexyl salicylate, bis-ethylhexyloxyphenol methoxyphenyl triazine, octocrylene, methylene bis-benzotriazolyl tetramethylbutylphenol, or phenylbenzimidazolesulfonic acid in addition to ethylhexyl methoxycinnamate, and isoamyl p-methoxycinnamate. The ultraviolet rays block index of the composition according to one embodiment may be at least SPF15, for example, SPF15 to SPF50, SPF30, SPF34, SPF45, or SPF50, or may be PA+, PA++ or PA+++.

The skin external composition may be formulated into a formulation applicable by application. Specifically, the skin external composition may be formulated as at least one selected from the group consisting of ointments, creams, lotions, emulsions, gels, cataplasmas, pastes, liniments, plasters, aromatic waters, aerosols, hydrogels, transcutaneous patch, and medicine-containing bandage.

the skin external composition may be suitably mixed, as necessary, with ingredients commonly used in the skin external preparation such as cosmetics and pharmaceuticals, for example, aqueous ingredients, oil ingredients, powder ingredients, opacifying agents, alcohols, humectants, thickeners, ultraviolet absorbing agents, whitening agents, preservatives, antioxidants, surfactants, fragrances, various skin nutrients, or a combination thereof. The skin external preparation may be obtained by suitably mixing metal blockers such as disodium edetate, trisodium edetate, sodium citrate, sodium polyphosphate, and sodium metaphosphate, gluconic acid, medicine such as caffeine, tannin, verapamil, licorice extract, glabridin, hot water extract of calin fruit, various herb medicines, tocopherol acetate, glycyrrhizic acid, tranexamic acid and derivatives thereof or salts thereof, vitamin C, magnesium ascorbic acid phosphate, ascorbic acid glucoside, arbutin, kojic acid, and sugars such as glucose, fructose and trehalose.

The composition may be configured to conceal the scar. The composition according to one embodiment includes the pigment and the silicone oil, so that the scar can be concealed and simultaneously the scar can be prevented or treated.

The scar prevention or treatment may be carried out by inhibiting moisture loss of the skin. Since the moisture loss increases in the damaged skin even when the wound heals, the damaged skin may proceeds into a scar as collagen synthesis becomes active. The composition forms a membrane on the scar, thereby reducing the moisture loss in a scar site, so that the scar can be prevented from being generated or a scar having already been generated can be treated.

Accordingly, due to the effects as described above, the composition can be useful for the prevention and/or treatment of scars and for the concealment of the scars.

Another aspect provides a pharmaceutical composition for preventing or treating a scar, which includes pigment and silicone oil.

The silicone oil, pigment, and scar are the same as described above.

The pharmaceutical composition may include a pharmaceutically acceptable diluent or carrier. The diluent may be lactose, corn starch, soybean oil, microcrystalline cellulose, mannitol, or lubricant such as magnesium stearate and talc, or a combination thereof. The carrier may be excipient, disintegrant, binder, a lubricant, or a combination thereof. The excipient may be microcrystalline cellulose, lactose, low-substituted hydroxycellulose, or a combination thereof. The disintegrant may be calcium carboxymethyl cellulose, sodium starch glycolate, anhydrous dibasic calcium phosphate, or a combination thereof. The binder may be polyvinylpyrrolidone, low-substituted hydroxypropylcellulose, hydroxypropylcellulose, or a combination thereof. The lubricant may be magnesium stearate, silicon dioxide, talc, or a combination thereof.

The pharmaceutical composition may be formulated into a parenteral administering formulation. The parenteral administering formulation may be injections or skin external preparations.

Another aspect provides a cosmetic composition including pigment and silicone oil to improve or alleviate scars.

The silicone oil, pigment, and scar are the same as described above.

The cosmetic composition may be prepared in various forms. For example, the cosmetic composition may be prepared in the form of emulsions, lotions, creams (oil-in-water, water-in-oil, multiphase), solutions, suspensions (anhydrous and aqueous), anhydrous products (oil and glycols), gels, masks, packs, powders and the like. In addition, the cosmetic composition herein may include an acceptable carrier in a cosmetic preparation. The expression "acceptable carrier in a cosmetic preparation" refers to a compound or composition already known and used that may be included in a cosmetic preparation or a compound or composition to be developed in the future, without toxicity, instability or irritation beyond a range adaptable by a body upon coming into contact with the skin. An amount of the carrier may be about 1 wt % to about 99.99 wt %, and preferably about 90 wt % to about 99.99 wt % by weight of the composition based on a total weight of the cosmetic composition herein. An example of the carrier may include alcohol, oil, surfactant, fatty acid, humectant, moisturizer, viscosity modifier, emulsion, stabilizer, sunscreen, color coupler, fragrance, and the like.

Another aspect provides a preparation method of a skin external composition, which includes: obtaining a first phase including silicone oil (S1); obtaining a second phase by mixing and dispersing the silicone oil and the pigment (S2); and mixing and dispersing the first phase and the second phase (S3).

The silicone oil, pigment, scar, and skin external composition are the same as described above.

In the specification herein, the term "dispersion" refers to a state in which solute particles are spread in a solvent or refers to an act of causing the state.

In the specification herein, the term "mixing and dispersing" may refer to an act of mixing and dispersing a sample.

In the above method, about 1% to about 30% by weight of the pigment based on the total weight of the skin external composition may be included, but it is not limited thereto.

Step S1, step S2 or step S3 may be performed at room temperature.

Step S1, step S2 or step S3 may be performed by dispersing, mixing, mixing and dispersing, grinding, or a combination thereof.

The dispersing or the mixing and dispersing may be performed by a milling process. The milling process may include, for example, roll milling, ball milling, bead milling, attrition milling, planetary milling, jet milling or ring milling. The roll milling process may be performed by, for example, a three-stage roller.

When the dispersion is performed by the milling process, the pigment may be split into smaller particles, or the pigment may uniformly spread in the silicone oil so that appliability or spreadability can be improved without aggregation.

The above method includes the steps of separately preparing the first phase including the silicone oil and the second phase including the silicone oil and the pigment instead of mixing the silicone oil and the pigment at once and then mixing and dispersing the same, so that the appliability or spreadability of the composition can be improved. In one embodiment, the second phase may be prepared by mixing the silicone oil and the pigment and then dispersing the same in a milling process.

Another aspect provides a method of preventing, improving, treating, or alleviating a scar, which includes: administering the composition including the pigment and the silicone oil to a subject. The composition is the same as described above.

The administration may be performed by any scheme known in the art. The administration may be performed, for example, through application onto a skin, or performed directly to the subject by any means through routes such as intravenous, intramuscular, transdermal, mucosal, intranasal, intratracheal or subcutaneous administration. The administration may be performed entirely or locally with respect to a body. The administration may be performed locally to a site of the wound or scar.

The subject may include a mammal such as human, cow, horse, pig, dog, sheep, goat, or cat.

Advantageous Effects

The composition according to one aspect can be stably formulated into a formulation suitable for application onto the skin while including the pigment and the silicone oil. In addition, the composition may form a membrane on the skin so that the formation of scar can be inhibited or a scar having already generated can be alleviated. In addition, the pigment stably dispersed in the composition can conceal the scar.

BEST MODE

Hereinafter, the embodiments of the present invention will be described in more detail by using examples. However, these examples are intended to illustrate one or more embodiments, but the scope of the present invention is not limited thereto.

Example 1 and Comparative Examples 1 to 4:
Preparation of Composition for Prevention or Treatment of Scars In order to prepare a composition for the prevention or treatment of scars the followings were performed. First, components of phase-A of Table 1 below were mixed at room temperature. Next, after mixing components of phase-B of Table 1, full dispersion was carried out using a three-stage roller (Kyoung Yong Machinery Co., Ltd.). After mixing phase-A with phase-B prepared as described above, full dispersion was carried out using the three-stage roller at room temperature, and thus the composition for prevention or treatment of the scars was prepared.

Specific components and contents of Example 1 and Comparative Examples 1 to 4 are shown in Table 1 below. Unless stated otherwise in the specification herein, content of each component is indicated as a weight percent.

TABLE 1

| Phase | Component | Comparative Example 1 | Comparative Example 2 | Comparative Example 3 | Comparative Example 4 | Example 1 |
|---|---|---|---|---|---|---|
| A | Dimethicone | 44.5275 | 40.4775 | 38.2275 | 31.4775 | 31.4775 |
|   | Polysilicon-11 | 14.8425 | 13.4925 | 12.7425 | 10.4925 | 10.4925 |
|   | Cyclopentasiloxane | 39.58 | 35.98 | 33.98 | 27.98 | 27.98 |
|   | Total | 98.95 | 89.95 | 84.95 | 69.95 | 69.95 |
| B | Titanium dioxide | 0.6435 | 6.435 | 6.435 | 12.87 | 12.87 |
|   | Zinc oxide | 0.18 | 1.8 | 1.8 | 3.6 | 3.6 |
|   | Iron oxide (CI 77492) | 0.0648 | 0.648 | 0.648 | 1.296 | 0.696 |
|   | Hydrogen dimethicone | 0.035 | 0.35 | 0.35 | 0.7 | 0.7 |
|   | Iron oxide (CI 77491) | 0.0276 | 0.276 | 0.276 | 0.552 | 0.324 |
|   | Iron oxide (CI 77499) | 0.027 | 0.27 | 0.27 | 0.54 | 0.264 |
|   | Aluminum hydroxide 0.0165 | 0.165 | 0.165 | 0.33 | 0.33 | |
|   | Diphenylsiloxyphenyltrimethicone | 0.00374 | 0.0374 | 0.0374 | 0.0748 | 0.04 |
|   | Triethoxysilylethylpolydimethyl-siloxyethylhexyldimethicone | 0.00124 | 0.0124 | 0.0124 | 0.0248 | 0.0136 |
|   | Bariumsulphate | 0.00061 | 0.0061 | 0.0061 | 0.0122 | 1.1392 |
|   | Dimethicone | 0.00001 | 0.0001 | 0.0001 | 0.0002 | 0.0232 |
|   | Cyclopentasiloxane | — | — | 3.2 | 6.4 | 6.4 |
|   | Cyclopentasiloxane | — | — | 1.8 | 3.6 | 3.6 |
|   | Tocopheryl acetate | 0.05 | 0.05 | 0.05 | 0.05 | 0.05 |
|   | Total | 1.05 | 10.05 | 15.05 | 30.05 | 30.05 |
|   | Total | 100 | 100 | 100 | 100 | 100 |

Experimental Example 1: Evaluation on Spreadability

Figure 1:
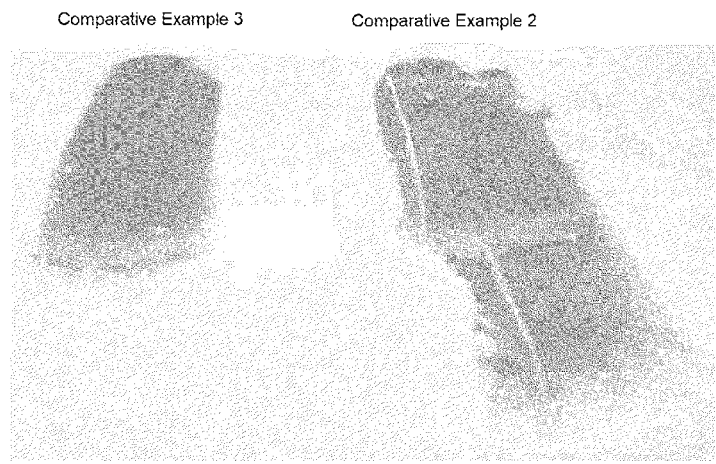
FIG. 1 is a photograph showing spreadability evaluation on compositions of comparative example 2 and comparative example 3 according to one embodiment.

In order to evaluate spreadability, compositions of Comparative Example 2 and Comparative Example 3 were evaluated by taking out the compositions with the same amount and applying the compositions onto a flat paper with the same force. FIG. 1 shows the spreadability evaluation result.

As shown in FIG. 1, it was confirmed that the composition of Comparative Example 3 has the excellent applicability and spreadability, because the composition of Comparative Example 3 was uniformly applied without clumping or agglomeration compared to the composition of Comparative Example 2.

Accordingly, it was confirmed that even when content of the silicone oil contained in the whole composition is the same, the pigment is dispersed in the composition stably and uniformly due to a process of dispersing the pigment into appropriate amounts of silicone oil by the milling process and then mixing the dispersion with remaining silicone oil, so that formulation becomes stable, the applicability and spreadability are improved, and the formulation is suitable to be applied to the skin.

Experimental Example 2: Evaluation on Scar Removability

In order to evaluate scar removability by concealing the scar, the same red marks were marked on one person's arm with a red pen; the same amount of the compositions of Comparative Example 1, Comparative Example 3, and Example 1 was applied to the marked portions or no composition was applied (control group); and the degree of removal of the red marks was checked. The resulted photographs are shown in FIG. 2.

Figure 2:
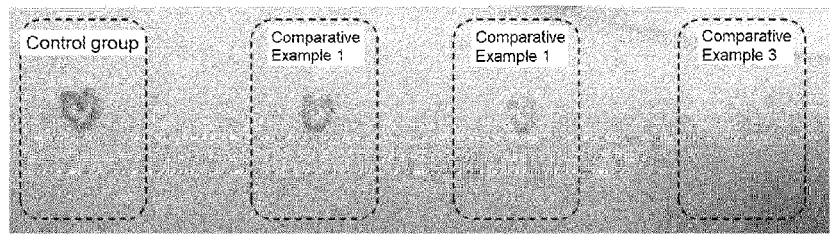
FIG. 2 is a photograph showing scar removal evaluation on compositions of comparative example 1, comparative example 3, and example 1 according to one embodiment.

As shown in FIG. 2, it was confirmed that the removal degrees of the red marks were excellent in a sequence of Comparative Example 1, Comparative Example 3, and Example 1.

Accordingly, it was confirmed that the composition of Example 1 contains the pigment so that the effect of concealing and removing the scar is excellent when applied to the skin.

Experimental Example 3: Evaluation on Scar Removability

Figure 3:
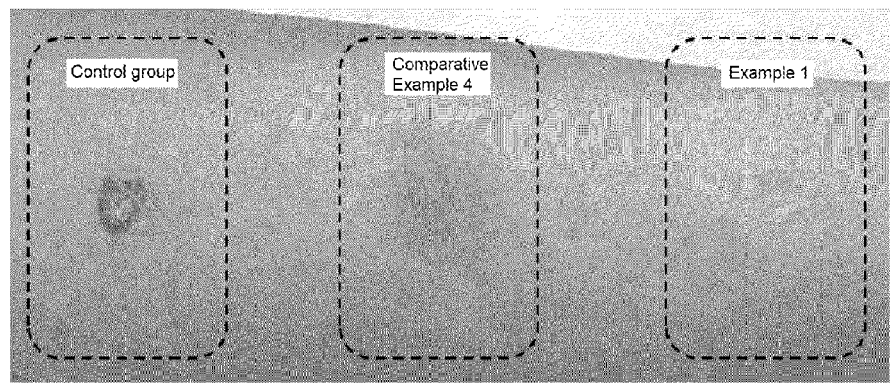
FIG. 3 is a photograph showing scar removal evaluation on compositions of comparative example 4 and example 1 according to one embodiment.

FIG. 3 shows photographs confirming the scar removability with application of the compositions of Comparative Example 4 and Example 1 or without application (control group), in the same manner as in Experiment Example 2.

As shown in FIG. 3, it was confirmed that the red mark appeared darkening when the composition of Comparative Example 4 is applied. In contrast, it was confirmed that the red mark was concealed properly and almost invisible as a result of the application of Example 1, and the pigment was deposited and thus became invisible.

Accordingly, it was confirmed that, because the skin looks black due to pigment when the pigment in the composition of Example 1 is excessively used, the composition of Example 1 using an appropriate amount of pigment has the excellent effect of scar removal and concealment.

Experimental Example 4: Evaluation on Scar Treatment Effect

In order to evaluate the scar treatment effect, the same scars were made on five mice, and sizes of the scars were measured. The compositions of Example 1, Comparative Examples 1 to 4 were applied to the scar sites once every three days for two months. The results of evaluating the scar treatment effect are shown in Table 2 below, in which sizes of the scars were measured after 2 months, and the scar size after application is calculated as a percentage of the scar size before application.

TABLE 2

| | Comparative Example 1 | Comparative Example 2 | Comparative Example 3 | Comparative Example 4 | Example 1 |
|---|---|---|---|---|---|
| Scar size | 10% | 12% | 11% | 12% | 10% |

As shown in Table 2, it was confirmed that the scars were reduced to about 10% within two months after applying the compositions of Comparative Examples 1 to 4 and Example 1. Accordingly, it was confirmed to exhibit an excellent scar healing effect when the compositions of Comparative Examples 1 to 4, and Example 1 include the silicone oil.

The invention claimed is:
1. A method for preparing a skin external composition, the method comprising:
   obtaining a first phase including a first silicone oil;
   obtaining a second phase comprising a second silicone oil and a pigment by mixing and dispersing the second silicone oil and the pigment, wherein the second silicone oil is distinct from the first silicone oil of the first phase; and
   mixing and dispersing the first phase and the second phase,
   wherein the silicone oils of the first and second phases include at least one selected from the group consisting of dimethicone, polysilicone-11, hydrogen dimethicone, cyclopentasiloxane and cyclohexasiloxane,
   wherein an amount of the total silicone oil of the first and second phases is in a range of 70% by weight to 85% by weight based on a total weight of the skin external composition,
   wherein the pigment includes at least one selected from the group consisting of titanium dioxide, zinc oxide, iron oxide and aluminum hydroxide,
   wherein an amount of the pigment is in a range of 10% by weight to 19% by weight based on a total weight of the skin external composition,
   and wherein the mixing and dispersing of the first and second phase is performed by a milling process.

* * * * *